United States Patent [19]

Enomoto et al.

[11] Patent Number: 5,156,668
[45] Date of Patent: Oct. 20, 1992

[54] BENZOXAZINYL-PYRAZOLES AND THEIR USE AS HERBICIDES

[75] Inventors: Masayuki Enomoto; Eiki Nagano, both of Hyogo; Ryo Sato; Masaharu Sakaki, both of Osaka, all of Japan

[73] Assignee: Sumitomo Chemical Company, Limited, Osaka, Japan

[21] Appl. No.: 593,972

[22] Filed: Oct. 9, 1990

[30] Foreign Application Priority Data

Oct. 12, 1989 [JP] Japan .................. 1-267839

[51] Int. Cl.$^5$ .............. A01N 43/84; C07D 413/04
[52] U.S. Cl. ............................. 71/92; 544/105
[58] Field of Search .............. 544/105; 71/92

[56] References Cited

U.S. PATENT DOCUMENTS

| | | | |
|---|---|---|---|
| 4,619,687 | 10/1986 | Haga et al. | 71/92 |
| 4,640,707 | 2/1987 | Nagano et al. | 71/96 |
| 4,752,326 | 6/1988 | Ohyama et al. | 71/92 |
| 4,877,444 | 10/1989 | Enomoto et al. | 71/92 |
| 4,885,024 | 12/1989 | Enomoto et al. | 71/92 |

FOREIGN PATENT DOCUMENTS

| | | |
|---|---|---|
| 0304935 | 8/1988 | European Pat. Off. . |
| 0311135 | 10/1988 | European Pat. Off. . |
| 0328001 | 8/1989 | European Pat. Off. . |
| 0334055 | 9/1989 | European Pat. Off. . |
| 1139580 | 11/1962 | Japan . |
| 29598 | 6/1963 | Japan . |
| 48130 | 9/1965 | Japan . |

*Primary Examiner*—Patricia L. Morris
*Attorney, Agent, or Firm*—Birch, Stewart, Kolasch & Birch

[57] ABSTRACT

A compound of the formula:

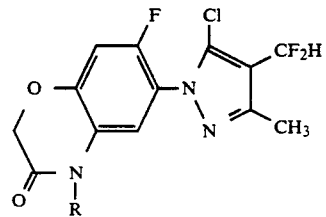

wherein R is a $C_1$–$C_5$ alkyl group, a $C_3$–$C_6$ alkenyl group, a $C_3$–$C_6$ alkynyl group or a $C_1$–$C_3$ alkoxy($C_1$–$C_3$)alkyl group, which is useful as a herbicide.

17 Claims, No Drawings

BENZOXAZINYL-PYRAZOLES AND THEIR USE AS HERBICIDES

The present invention relates to benzoxazinyl-pyrazoles, and their production and use. More particularly, it relates to benzoxazinyl-pyrazoles having strong herbicidal potency and showing noticeable selectivity between crop plants and weeds.

JP-B-40-19958 and JP-B-42-14833 disclose some pyrazole derivatives. Also, EP-A-334055 discloses some benzoxadinyl-pyrazole derivatives having herbicidal activity. However, these known compounds are not sufficient in their herbicidal activity or have poor selectivity between crop plants and weeds. Thus, they can hardly be said to be satisfactory herbicides.

An extensive study has been made seeking satisfactory herbicides, and as the result, it has been found that benzoxazinyl-pyrazoles of the formula:

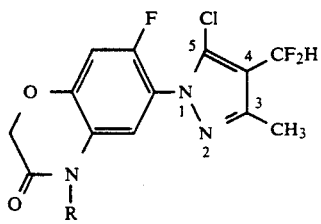

wherein R is a $C_1$–$C_5$ alkyl group, a $C_3$–$C_6$ alkenyl group, a $C_3$–$C_6$ alkynyl group or a $C_1$–$C_3$ alkoxy($C_1$–$C_3$)alkyl group, exhibit strong herbicidal potency with noticeable selectivity between crop plants and weeds. This invention is based on the above finding.

The benzoxazinyl-pyrazoles (I) produce generally strong herbicidal activity against a wide variety of weeds including broad-leaved weeds, Graminaceous weeds, Commelinaceous weeds and Cyperaceous weeds in agricultural plowed fields by foliar or soil treatment, preferably soil treatment, without producing any material phytotoxicity on various agricultural crops such as corn, wheat, barley, rice plant, soybean, sugar beet and cotton, preferably corn and soybean. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*) hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), purple deadnettle (*Lamium purpureum*), etc. Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), bermudagrass (*Cynodon dactylon*), etc. Examples of the Commelinaceous weeds include asiatic dayflower (*Commelina communis*), etc. Examples of the Cyperaceous weeds include rice flatsedge (*Cyperus iria*), etc.

The benzoxazinyl-pyrazoles (I) are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as hardstem bulrush (*Scirpus juncoides*) and needle spikerush (*Eleocharis acicularis*), and others such as monochoria (*Monochoria vaginalis*) and arrowhead (*Sagittaria pygmaea*) without producing any phytotoxicity to rice plants on flooding treatment.

The structural characteristics of the benzoxazinyl-pyrazoles (I) include certain specific substituents at the 3-, 4- and 5-positions on the pyrazole ring, a methyl group at the 3-position, a difluoromethyl group at the 4-position and a chlorine atom at the 5-position. Due to the presence of such specific substituents as mentioned above on the pyrazole ring, the resulting benzoxazinyl-pyrazoles (I) exhibit highly enhanced herbicidal potency and highly improved selectivity.

Among the benzoxazinyl-pyrazoles (I), preferred are those wherein R is an n-propyl group, a 2-propenyl group, a propargyl group or a methoxymethyl group. More preferred are those wherein R is a propargyl group.

The benzoxazinyl-pyrazoles (I) of the invention are produced by reacting a compound of the formula:

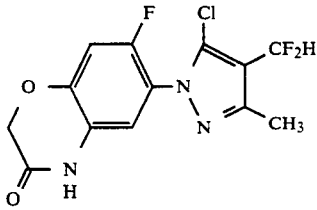

with a compound of the formula:

R—X (III)

wherein R is as defined above and X is a leaving group such as a halogen atom (e.g. chlorine, bromine, iodine) or a sulfonyloxy group (e.g. methanesulfonyloxy, ethanesulfonyloxy, benzenesulfonyloxy, p-toluenesulfonyloxy).

The reaction is usually effected in the presence of a base in an inert solvent at a temperature of about 0 to 100° C. for a period of about 0.5 to 10 hours. Normally, the compound (III) and the base are used, respectively, in amounts of 1 to 2 equivalents and of 1 to 2 equivalents to one equivalent of the compound (II). Examples of the inert solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), fatty acids (e.g. formic acid, acetic acid, oleinic acid), esters (e.g. ethyl formate, ethyl acetate, butyl acetate, diethyl carbonate), nitro compounds (e.g. nitroethane, nitrobenzene), nitriles (e.g. acetonitrile, isobutyro-nitrile), tertiary amines (e.g. pyridine, triethylamine, N,N-diethylanilie, tributylamine, N-methylmorpholine), acid amides (e.g. formamide, N,N-dimethylformamide, acetamide), sulfur compounds (e.g. dimethylsulfoxide, sulforan), aqueous ammonia, water, etc., and their mixtures. As the base, there may be employed an organic base (e.g. pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

Upon termination of the reaction, the reaction mixture is subjected to post-treatment by a per se conventional procedure. For instance, the reaction mixture is poured into water, and the precipitated crystals are collected by filtration. Further, for instance, the reaction mixture is admixed with water and extracted with an organic solvent, if necessary, followed by concentration to obtain the objective product as crystals. When desired, the collected product may be purified by a per se conventional procedure such as chromatography, distillation or recrystallization.

Still, some of the benzoxazinyl-pyrazoles (I) may have optical isomers due to the asymmetric carbon atom, and this invention covers those optical isomers.

A typical embodiment for production of the benzoxazinyl-pyrazoles (I) is illustratively shown in the following Example.

EXAMPLE 1

Production of Compound No. 3:

To a solution of 5-chloro-4-difluoromethyl-1-[7-fluoro-2H-1,4-benzoxazin-3(4H)-on-6-yl]-3-methyl-pyrazole (2.0 g) in dimethylformamide (10 g), propargyl bromide (0.8 g) and potassium carbonate (1.6 g) were added, and the resultant mixture was stirred at 40 to 80° C for 3 hours. The reaction mixture was poured into water, and the precipitated crystals were collected by filtration, washed with water and dried, followed by purification by column chromatography to give the objective compound (1.0 g) as white crystals. m.p., 181-183° C.

$^1$H-NMR δ(ppm) (CDCl$_3$, 60 MHz): 2.05 (t, J=2 Hz, 1H), 2.20 (s, 3H), 4.50 (d, J=2 Hz, 2H), 4.51 (s, 3H), 6.40 (t, J =5.4 Hz, 1H), 6.78 (d, J=11 Hz, 1H), 6.98 (d, J=7 Hz, 1H).

In the same manner as above, the benzoxazinyl-pyrazoles (I) as shown in Table 1 are obtainable.

TABLE 1

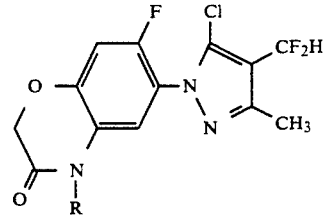

| Compound No. | R | Melting point (°C.) |
|---|---|---|
| 1 | n-C$_3$H$_7$ | 104-105 |
| 2 | CH$_2$CH=CH$_2$ | 136.5-137 |
| 3 | CH$_2$C≡CH | 181-183 |

TABLE 1-continued

| Compound No. | R | Melting point (°C.) |
|---|---|---|
| 4 | CH$_2$OCH$_3$ | 110-113 |

The compound (II) as the starting material in the above process can be produced according to the following scheme:

(IV) → (V) → (VI) → (VII) → (VIII) → (II)

Practical embodiments for production of the intermediate compounds, i.e. Compounds (V), (VI), (VII), (VIII) and (II), are shown in the following examples.

EXAMPLE 2

Production of Compound (V):

To a solution of Compound (IV) (2.0 g) in dimethylformamide (10 g), phosphorus oxychloride (3.5 g) was added, and the resultant mixture was stirred at 80 to 100° C. for 3 hours. After completion of the reaction, the reaction mixture was poured into water, and the precipitated crystals were collected by filtration, washed with water and dried, followed by purification by column chromatography to give the objective compound (1.0 g) as white crystals. m.p., 121-122° C.

EXAMPLE 3

Production of Compound (VI):

To a solution of Compound (V) (1.0 g) in dichloromethane (10 g), N,N-diethylaminosulfur trifluoride (3.8 g) was added, and the resultant mixture was stirred at room temperature overnight. After completion of the reaction, the reaction mixture was poured into water. The organic layer was separated, washed with water and dried, followed by purification by column chromatography to give the objective compound (0.7 g) as white crystals. m.p., 89-91° C.

EXAMPLE 4

Production of Compound (VII):

To a solution of Compound (VI) (0.7 g) in conc. sulfuric acid (10 g), conc. nitric acid (0.4 g) was added while cooling with ice, and the resultant mixture was stirred at a temperature below 10° C. for 3 hours. After completion of the reaction, the reaction mixture was poured into water, and the precipitated crystals were collected by filtration, washed with water and dried, followed by purification by column chromatography to give the objective compound (0.7 g) as white crystals. m.p., 81-83° C.

EXAMPLE 5

Production of Compound (VIII):

To a solution of Compound (VII) (0.5 g) in dioxane (10 g), potassium fluoride (1.5 g) and butyl glycolate (0.5 g) were added, and the resultant mixture was refluxed for 3 hours. After completion of the reaction, the reaction mixture was poured into water and extracted with ether. The extract was washed with water, dried and concentrated, followed by purification by column chromatography to give the objective compound (0.6 g) as white crystals. m.p., 142-144° C.

EXAMPLE 6

Production of Compound (II):

To a solution of Compound (VIII) (0.5 g) in 80% aqueous acetic acid (5 g), iron powders (0.5 g) were added, and the resultant mixture was heated at 80 to 100° C. for 3 hours. After completion of the reaction, the reaction mixture was combined with ethyl acetate (10 g). Insoluble materials were removed by filtration, and the filtrate was washed with water, dried and concentrated, followed by purification by column chromatography to give the objective compound (0.2 g) as white crystals. m.p., 270-274° C.

Still, Compound (IV) can be produced by reacting 2,4-difluorophenylhydrazine with ethyl acetoacetate in acetic acid at a temperature of 50 to 100° C.

For the practical usage of the benzoxazinylpyrazoles (I), they are usually formulated with conventional solid or liquid carriers or diluents as well as surface active agents or auxiliary agents into conventional preparation forms such as emulsifiable concentrates, wettable powders, suspensions and granules. The content of the benzoxazinyl-pyrazoles (I) as the active ingredient in such preparation forms is normally within a range of about 0.02 to 80% by weight, preferably of about 0.05 to 70% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), vegetable oil (e.g. soybean oil, cotton seed oil), dimethylsulfoxide, N,N-dimethylformamide, acetonitrile, water, etc.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one in Table 1.

FORMULATION EXAMPLE 1

Fifty parts of any one of Compound Nos. 1 to 4, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of Compound No. 1 or 2, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

FORMULATION EXAMPLE 3

Two parts of Compound No. 3 or 4, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 3 or 4 are mixed with 3 parts of polyoxyethylene sorbitan monooleate, 3 parts of carboxymethyl cellulose and 69 parts of water and pulverized until the particle size of the mixture becomes less than 5 microns to obtain a suspension.

The benzoxazinyl-pyrazole (I) thus formulated in any suitable preparation form is useful for pre-emergence or post-emergence control of undesired weeds by soil or foliar treatment as well as flood fallowing treatment. These treatments include application to the soil surface prior to or after planting, incorporation into the soil prior to planting or transplanting, etc. The foliar treatment may be effected by spraying the herbicidal composition containing the benzoxazinyl-pyrazole (I) over the top of plants. It may also be applied directly to the weeds if care is taken to keep the chemical off the crop foliage.

The benzoxazinyl-pyrazole (I) may be used together with any other herbicide to improve its activity as a herbicide, and in some cases, a synergistic effect can be expected. Further, it may be applied in combination with an insecticide, an acaricide, a nematocide, a fungicide, a plant growth regulator, a fertilizer, a soil improver, etc. It is also useful as a herbicide to be employed for orchards, pasture land, lawns, forests, non-agricultural fields, etc.

The dosage of the benzoxazinyl-pyrazole (I) may vary depending on the prevailing weather conditions, the formulation used, the prevailing season, the mode of application, the soil involved, the crop and weed species, etc. Generally, however, the dosage is from about 0.01 to 100 grams, preferably from about 0.05 to 50 grams, of the active ingredient per are. The practical dosage of the benzoxazinyl-pyrazole (I) by soil treatment in a field of soybean may be from about 0.1 to 2 grams per are. The herbicidal composition of the invention formulated in the form of an emulsifiable concentrate, a wettable powder or a suspension may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data on the benzoxazinyl-pyrazoles (I) as a herbicide will be illustratively shown in the following Examples, wherein the phytotoxicity to crop plants and the herbicidal activity on weeds were observed visually as to the degree of germination as well as the growth inhibition, and rated with an index of 0, 1, 2, 3, 4 or 5, the numeral "0" indicating no material difference as seen in comparison with the untreated plants, and the numeral "5" indicating the complete inhibition or death of the test plants.

The compounds as shown in Table 2 were used for comparison.

TABLE 2

| Compound No. | Structure | Remarks |
|---|---|---|
| A | [structure] | JP-B-40-19958 |
| B | [structure] | JP-B-42-14833 |
| C | [structure] | Chloronitrofen |
| D | [structure] | EP-A-0334055 |
| E | [structure] | Synthesized for comparison; m.p., 154–155° C. |
| F | [structure] | Synthesized for comparison; m.p., 173–175° C. |
| G | [structure] | Synthesized for comparison; m.p., 107–108° C. |
| H | [structure] | Synthesized for comparison; m.p., 141–144° C. |
| I | [structure] | Synthesized for comparison; m.p., 127–129° C. |

TEST EXAMPLE 1

Cylindrical plastic pots (diameter, 10 cm; height, 10 cm) were filled with upland field soil, and the seeds of Japanese millet, oats, tall morning glory and velvet leaf were sown therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 3.

TABLE 3

| Compound No. | Dosage (g/are) | Herbicidal activity | | | |
|---|---|---|---|---|---|
| | | Japanese millet | Oats | Tall morning-glory | Velvet-leaf |
| 2 | 5 | 5 | 5 | 5 | 5 |
| 3 | 5 | 5 | 5 | 5 | 5 |
| 4 | 5 | 5 | 5 | 5 | 5 |
| A | 5 | 0 | 0 | 0 | 0 |
| B | 5 | 0 | 0 | 0 | 0 |
| C | 5 | 0 | 0 | 0 | 0 |

TEST EXAMPLE 2

Cylindrical plastic pots (diameter, 10 cm; height, 10 cm) were filled with upland field soil, and the seeds of Japanese millet, oats, radish and velvetleaf were sown therein and cultivated in a greenhouse for 10 days. A designated amount of the test compound formulated in an emulsifiable concentrate as in Formulation Example 2 was diluted with water containing a spreading agents, and the dilution was sprayed over the foliage of the test plant by means of a small hand sprayer at a spray volume of 10 liters per are. The test plants were further grown in a greenhouse for 20 days, and the herbicidal activity was examined. The results are shown in Table 4.

TABLE 4

Herbicidal activity

| Compound No. | Dosage (g/are) | Japanese millet | Oats | Radish | Velvet-leaf |
|---|---|---|---|---|---|
| 1 | 2.5 | 5 | 4 | 5 | 5 |
| 2 | 2.5 | 5 | 5 | 5 | 5 |
| 3 | 2.5 | 5 | 5 | 5 | 5 |
| A | 2.5 | 1 | 0 | 0 | 3 |
| B | 2.5 | 0 | 0 | 0 | 0 |

TEST EXAMPLE 3

Cylindrical plastic pots (diameter, 8 cm; height, 12 cm) were filled with paddy field soil, and the seeds of barnyardgrass (*Echinochloa oryzicola*), broad-leaved weeds (i.e. common falsepimpernel, indian toothcup, rewarterwort) were sown therein at a depth of 1 to 2 cm. Water was poured therein to make a flooded condition, and the test plants were grown in a greenhouse. Six days (at that time weeds began to germinate) thereafter, a designated amount of the test compound formulated in an emulsifiable concentrate as in Formulation Example 2 and diluted with water (5 ml) was applied to the pots by perfusion. The test plants were grown for an additional 20 days in the greenhouse, and the herbicidal activity was examined. The results are shown in Table 5.

TABLE 5

| Compound No. | Dosage (g/are) | Herbicidal activity | |
|---|---|---|---|
| | | Barnyard-grass | Broad-leaved weed |
| 1 | 1.25 | 5 | 5 |
| 2 | 1.25 | 5 | 5 |
| 3 | 1.25 | 5 | 5 |
| 4 | 1.25 | 5 | 5 |
| A | 1.25 | 0 | 0 |
| B | 1.25 | 0 | 0 |

TEST EXAMPLE 4

Vats (33 cm × 23 cm × 11 cm) were filled with upland field soil, and the seeds of soybean, corn, rice plant, tall morningglory, velvetleaf, black nightshade, redroot pigweed and green foxtail were sown therein at a depth of 1 to 2 cm. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in the greenhouse for 20 days, and the herbicidal activity and phytotoxicity were examined. The results are shown in Table 6.

TABLE 6

| Compound No. | Dosage (g/are) | Phytotoxicity | | | Herbicidal activity | | | | |
|---|---|---|---|---|---|---|---|---|---|
| | | Soybean | Corn | Rice plant | Tall morningglory | Velvetleaf | Black nightshade | Redroot pigweed | Green foxtail |
| 3 | 1.25 | 1 | 0 | 1 | 5 | 5 | 5 | 5 | 5 |
|   | 0.63 | 0 | 0 | 0 | 4 | 5 | 5 | 5 | 4 |
| A | 1.25 | — | 0 | 0 | 1 | 3 | 1 | 0 | 2 |
|   | 0.63 | 0 | 0 | 0 | 0 | 1 | 0 | 0 | 0 |
| B | 1.25 | 0 | 0 | 0 | 0 | 0 | 0 | 0 | 0 |
|   | 0.63 | 0 | 0 | 0 | 0 | 0 | 0 | 0 | 0 |
| C | 1.25 | 0 | 0 | 0 | 0 | 0 | 0 | 0 | 0 |
|   | 0.63 | 0 | 0 | 0 | 0 | 0 | 0 | 0 | 0 |

TEST EXAMPLE 5

Vats (33 cm x 23 cm x 11 cm) were filled with upland field soil, and the seeds of wheat, barley, sugar beet, pale smartweed, common chichweed, persian speedwell, common lambsquarters and field pansy were sown therein at a depth of 1 to 2 cm. A designated amount of the test compound formulated in an emulsifiable concentrate as in Formulation Example 2 was diluted with water, and the dilution was sprayed onto the surface of the test plants by means of a small hand sprayer at a spray volume of 10 liters per are. The test plants were grown in a greenhouse for 27 days, and the herbicidal activity and the phytotoxicity were examined. The results are shown in Table 7.

TABLE 7

| Compound No. | Dosage (g/are) | Phytotoxicity | | | Herbicidal activity | | | | |
|---|---|---|---|---|---|---|---|---|---|
| | | Wheat | Barley | Sugar beet | Pale smartweed | Common chickweed | Persian speedwell | Common lambsquarters | Field pansy |
| 3 | 2.5 | 0 | 1 | 1 | 5 | 5 | 5 | 5 | 5 |

TABLE 7-continued

| Compound No. | Dosage (g/are) | Phytotoxicity | | | Herbicidal activity | | | | |
| --- | --- | --- | --- | --- | --- | --- | --- | --- | --- |
| | | Wheat | Barley | Sugar beet | Pale smartweed | Common chickweed | Persian speedwell | Common lambsquarters | Field pansy |
| | 1.25 | 0 | 0 | 1 | 5 | — | — | 5 | 5 |
| A | 2.5 | 0 | 0 | 0 | 3 | 0 | 0 | 0 | 3 |
| | 1.25 | 0 | 0 | 0 | 2 | 0 | 0 | 0 | 0 |
| B | 2.5 | 0 | 0 | 0 | 0 | 0 | 0 | 0 | 0 |
| | 1.25 | 0 | 0 | 0 | 0 | 0 | 0 | 0 | 0 |
| C | 2.5 | 0 | 0 | 0 | 0 | 0 | 0 | 0 | 0 |
| | 1.25 | 0 | 0 | 0 | 0 | 0 | 0 | 0 | 0 |

TEST EXAMPLE 6

Vats (33 cm × 23 cm × 11 cm) were filled with upland field soil, and the seeds of soybean, corn, tall morning-glory, velvetleaf, black nightshade, prickly sida were sown therein and cultivated for 18 days in a greenhouse. A designated amount of the test compound formulated in an emulsifiable concentrate as in Formulation Example 2 was diluted with water, and the dilution was sprayed over the foliage of the test plants by means of a small hand sprayer at a spray volume of 10 liters per are. The test plants were further grown in the greenhouse for 20 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 8.

TABLE 8

| Compound No. | Dosage (g/are) | Phytotoxicity | | Herbicidal activity | | | |
| --- | --- | --- | --- | --- | --- | --- | --- |
| | | Soybean | Corn | Tall morning-glory | Velvet leaf | Black nightshade | Prickly sida |
| 3 | 0.32 | 1 | 1 | 5 | 5 | 5 | 5 |
| | 0.16 | 1 | 1 | 4 | 5 | 5 | 5 |
| A | 0.32 | 0 | 0 | 0 | 3 | 0 | 0 |
| | 0.16 | 0 | 0 | 0 | 2 | 0 | 0 |
| B | 0.32 | 0 | 0 | 0 | 0 | 0 | 0 |
| | 0.16 | 0 | 0 | 0 | 0 | 0 | 0 |
| C | 0.32 | — | 0 | 0 | 1 | 0 | 1 |
| | 0.16 | — | 0 | 0 | 0 | 0 | 0 |

TEST EXAMPLE 7

Wagner's pots (1/5000 are) were filled with paddy field soil, and the seeds of barnyardgrass (*Echinochloa oryzicola*), broad-leaved weeds (i.e. common falsepimpernel, indian toothcup, warterwort) were sown therein at a depth of 1 to 2 cm. Water was poured therein to make a flooded condition, rice seedlings of 3-leaf stage were transplanted therein, and the test plants were grown in a greenhouse. Eleven days (at the 2 leaf stage of barnyardgrass) thereafter, a designated amount of the test compound formulated in an emulsifiable concentrate as in Formulation Example 2 and diluted with water (10 ml) was applied to the pots by perfusion. The test plants were grown for an additional 20 days in the greenhouse, and the herbicidal activity and phytotoxicity were examined. The results are shown in Table 9. At the time of the treatment, the depth of water in the pots was kept at 4 cm and following two days, water was let leak a volume corresponding to a 3 cm depth per day.

TABLE 9

| Compound No. | Dosage (g/are) | Phytotoxicity Rice plant | Herbicidal activity | |
| --- | --- | --- | --- | --- |
| | | | Barnyard-grass | Broad-leaved weeds |
| 3 | 0.32 | 1 | 5 | 5 |
| | 0.16 | 1 | 5 | 5 |
| C | 0.32 | 0 | 0 | 0 |
| | 0.16 | 0 | 0 | 0 |

TEST EXAMPLE 8

Vats (11 cm × 15 cm × 7 cm) were filled with upland field soil, and the seeds of soybean, prickly sida, velvetleaf and black nightshade were sown therein at a depth of 1 to 2 cm. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity and phytotoxicity were examined. The result are shown in Table 10.

TABLE 10

| Compound No. | Dosage (g/are) | Phytotoxicity Soybean | Herbicidal activity | | |
| --- | --- | --- | --- | --- | --- |
| | | | Prickly sida | Velvet-leaf | Black nightshade |
| 3 | 0.63 | 0 | 5 | 5 | 5 |
| | 0.32 | 0 | 3 | 5 | 4 |
| D | 0.63 | 0 | 0 | 0 | 0 |
| | 0.32 | 0 | 0 | 0 | 0 |
| E | 0.63 | 0 | 0 | 0 | 0 |
| | 0.32 | 0 | 0 | 0 | 0 |
| F | 0.63 | 0 | 3 | 3 | 3 |
| | 0.32 | 0 | 1 | 2 | 1 |
| G | 0.63 | 0 | 0 | 0 | 0 |
| | 0.32 | 0 | 0 | 0 | 0 |
| H | 0.63 | 0 | 0 | 0 | 0 |
| | 0.32 | 0 | 0 | 0 | 0 |
| I | 0.63 | 0 | 0 | 0 | 0 |
| | 0.32 | 0 | 0 | 0 | 0 |

What is claimed is:
1. A compound of the formula:

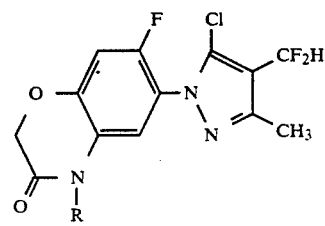

wherein R is a $C_1-C_5$ alkyl group, a $C_3-C_6$ alkenyl group, a $C_3-C_6$ alkynyl group, or a $C_1-C_3$ alkoxy $(C_1-C_3)$ alkyl group.

2. The compound according to claim 1, wherein R is an n-propyl group, a 2-propenyl group, a propargyl group, or a methoxymethyl group.

3. The compound according to claim 1, wherein R is a propargyl group.

4. A herbicidal composition, which comprises as an active ingredient a herbicidally effective amount of the compound according to claim 1, and an inert carrier or diluent.

5. A method for exterminating harmful weeds, which comprises applying a herbicidally effective amount of the compound according to claim 1 and an inert carrier or diluent to the area where undesired weeds grow or will grow.

6. The method according to claim 5, wherein the application is effected in a field of soybean, corn or wheat by soil treatment.

7. The method according to claim 5, wherein the application is effected in a field of soybean by soil treatment.

8. The herbicidal composition of claim 4, wherein said composition is in a form selected from the group consisting of an emulsifiable concentrate, a wettable powder, a suspension, and granules.

9. The herbicidal composition of claim 4, wherein said compound is present in an amount in the range of from about 0.02% to about 80% by weight.

10. The herbicidal composition of claim 4, wherein said compound is present in an amount in the range of from about 0.05% to about 70% by weight.

11. The herbicidal composition of claim 4, wherein said carrier or diluent is a solid material selected from the group consisting of fine powder or granules or kaolin clay, attapulgite clay, beutonite, terra alba, pyrophyllite, talc, diatomaceous earth, calcite, walnut powders, urea, ammonium sulfate, and synthetic hydrous silicate.

12. The method according to claim 5, wherein said applying is conducted by soil or foliar treatment, or by flood fallowing treatment.

13. The method according to claim 12, wherein said soil treatment is conducted by applying said compound to the soil surface prior to or after planting, or by incorporating said compound into said soil prior to planting or transplanting.

14. The method according to claim 12, wherein said foliar treatment is conducted by spraying or direct application.

15. The method according to claim 5, wherein said area is selected from the group consisting of an orchard, a pasture, a lawn, a forest, or a non-agricultural field.

16. The method according to claim 5, wherein the dosage of said compound is in the range of from about 0.01 to about 100 grams per are.

17. The method according to claim 5, wherein the dosage of said compound is in the range of from about 0.05 to about 50 grams per are.

* * * * *